(12) United States Patent
Stoller et al.

(10) Patent No.: US 8,618,173 B2
(45) Date of Patent: *Dec. 31, 2013

(54) INSECTICIDAL COMPOUNDS

(75) Inventors: Andre Denis Stoller, Stein (CH); Pierre Joseph Marcel Jung, Stein (CH); Christopher Richard Ayles Godfrey, Stein (CH); William Lutz, Stein (CH); Peter Maienfisch, Stein (CH); Werner Zambach, Stein (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 618 days.

This patent is subject to a terminal disclaimer.

(21) Appl. No.: 12/738,224

(22) PCT Filed: Oct. 13, 2008

(86) PCT No.: PCT/EP2008/008643
§ 371 (c)(1),
(2), (4) Date: Apr. 15, 2010

(87) PCT Pub. No.: WO2009/049845
PCT Pub. Date: Apr. 23, 2009

(65) Prior Publication Data
US 2010/0240712 A1    Sep. 23, 2010

(30) Foreign Application Priority Data

Oct. 17, 2007    (GB) .................................. 0720320.1

(51) Int. Cl.
*A01N 37/18*    (2006.01)
(52) U.S. Cl.
USPC .......................................... 514/616; 514/919
(58) Field of Classification Search
None
See application file for complete search history.

(56) References Cited

U.S. PATENT DOCUMENTS 6,194,418 B1    2/2001    Seitz et al.

FOREIGN PATENT DOCUMENTS

| EP | 1538138 | 6/2005 |
|---|---|---|
| EP | 1661886 | 5/2006 |
| EP | 1714958 | 10/2006 |
| WO | 9708135 | 3/1997 |

OTHER PUBLICATIONS

Patani et al., Chemical Reviews, "Bioisosterism: A Rational Approach in Drug Design", 1996, vol. 96, pp. 3147-3176.*

* cited by examiner

*Primary Examiner* — Savitha Rao
*Assistant Examiner* — Gregg Polansky
(74) *Attorney, Agent, or Firm* — R. Kody Jones

(57) ABSTRACT

Novel aromatic compounds of formula (I):

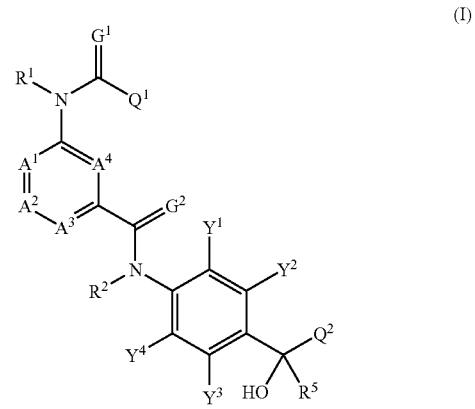

wherein $A^1, A^2, A^3, A^4, R^1, R^2, R^5, G^1, G^2, Q^1, Q^2, Y^1, Y^2, Y^3$ and $Y^4$ are as defined in claim 1; or a salt or N-oxide thereof. Furthermore, the present invention relates to processes for preparing compounds of formula (I), to insecticidal, acaricidal, nematicidal or molluscicidal compositions comprising them and to methods of using them to combat and control insect, acarine, nematode or mollusc pests.

13 Claims, No Drawings

INSECTICIDAL COMPOUNDS

This application is a 371 of International Application No. PCT/EP2008/008643 filed Oct. 13, 2008, which claims priority to GB 0720320.1 filed Oct. 17, 2007, the contents of which are incorporated herein by reference.

The present invention relates to certain bisamide derivatives, to processes and intermediates for preparing them, to insecticidal, acaricidal, nematicidal or molluscicidal compositions comprising them and to methods of using them to combat and control insect, acarine, nematode or mollusc pests.

Bisamide derivatives with insecticidal properties are disclosed, for example, in EP 1,714,958, JP 2006/306771, WO 06/137376, WO 06/137395 and WO 07/017,075.

It has now surprisingly been found that bisamide derivatives which are substituted by a certain carbinol substituents have insecticidal properties.

The present invention therefore provides a compound of formula (I):

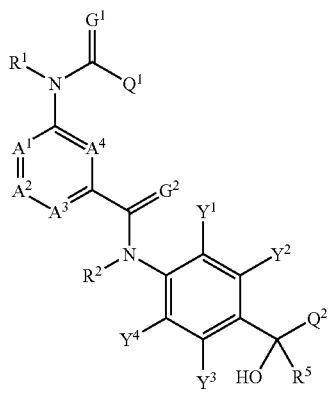

wherein
$A^1$, $A^2$, $A^3$ and $A^4$ are independently of one another C—X or nitrogen, provided that no more than two of $A^1$, $A^2$, $A^3$ and $A^4$ are nitrogen;
each X is independently hydrogen, halogen, cyano, $C_1$-$C_4$alkyl, $C_1$-$C_4$haloalkyl or $C_1$-$C_4$alkoxy;
$R^1$ and $R^2$ are independently of one another hydrogen, $C_1$-$C_4$alkyl or $C_1$-$C_4$alkylcarbonyl-;
$G^1$ and $G^2$ are independently of one another oxygen or sulfur;
$Q^1$ is aryl or aryl substituted by one to five substituents $R^3$, which may be the same or different, or $Q^1$ is heterocyclyl or heterocyclyl substituted by one to five substituents $R^3$, which may be the same or different;
$Q^2$ is aryl or aryl substituted by one to five substituents $R^4$, which may be the same or different, or $Q^2$ is heterocyclyl or heterocyclyl substituted by one to five substituents $R^4$, which may be the same or different;
each $R^3$ is independently halogen, cyano, nitro, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halocycloalkyl, hydroxy, $C_1$-$C_3$alkoxy, $C_1$-$C_3$haloalkoxy, $C_1$-$C_3$alkylthio-, $C_1$-$C_3$haloalkylthio-, $C_1$-$C_3$alkylsulfinyl-, $C_1$-$C_3$haloalkylsulfinyl-, $C_1$-$C_3$alkylsulfonyl-, $C_1$-$C_3$haloalkylsulfonyl-, N—$C_1$-$C_4$alkylamino-, N,N-di-($C_1$-$C_4$alkyl)amino-, $C_1$-$C_4$alkylcarbonyl-, $C_1$-$C_4$alkylcarbonyloxy-, $C_1$-$C_4$alkoxycarbonyl-, $C_1$-$C_4$alkylcarbonylamino- or phenyl;

each $R^4$ is independently halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halocycloalkyl, hydroxy, $C_1$-$C_3$alkoxy or $C_1$-$C_3$haloalkoxy;
$R^5$ is $C_1$-$C_4$ perfluoroalkyl;
$Y^1$ and $Y^4$ are independently of each other halogen, cyano, $C_1$-$C_4$alkyl, $C_1$-$C_4$haloalkyl, $C_1$-$C_4$alkoxy-$C_1$-$C_4$alkyl-, $C_1$-$C_3$alkylthio-, $C_1$-$C_3$haloalkylthio-, $C_1$-$C_3$alkylsulfinyl-, $C_1$-$C_3$haloalkylsulfinyl-, $C_1$-$C_3$alkylsulfonyl- or $C_1$-$C_3$haloalkylsulfonyl-; and
$Y^2$ and $Y^3$ are independently of each other hydrogen, halogen or $C_1$-$C_4$alkyl;
or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkylcarbonyl, alkoxycarbonyl) is a straight or branched chain and is, for example, methyl, ethyl, n-propyl, iso-propyl, n-butyl, sec-butyl, iso-butyl or tert-butyl. The alkyl groups are preferably $C_1$ to $C_6$ alkyl groups, more preferably $C_1$-$C_4$ and most preferably $C_1$-$C_3$ alkyl groups.

Alkenyl and alkynyl moieties (either alone or as part of a larger group) can be in the form of straight or branched chains, and the alkenyl moieties, where appropriate, can be of either the (E)- or (Z)-configuration. Examples are vinyl, allyl and propargyl. The alkenyl and alkynyl groups are preferably $C_2$ to $C_6$ alkenyl or alkynyl groups, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, trifluoromethyl, chlorodifluoromethyl, 2,2,2-trifluoro-ethyl or 2,2-difluoro-ethyl. Perfluoroalkyl groups (either alone or as part of a larger group, such as perfluoroalkylthio) are a particular type of haloalkyl group; they are alkyl groups which are completely substituted with fluorine atoms and are, for example, trifluoromethyl, pentafluoroethyl or heptafluoro-prop-2-yl.

Haloalkenyl and haloalkynyl groups (either alone or as part of a larger group) are alkenyl and alkynyl groups, respectively, which are substituted with one or more of the same or different halogen atoms and are, for example, 2,2-difluorovinyl, 1,2-dichloro-2-fluoro-vinyl or 1-chloro-prop-2-yn-1-yl-.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methyl-cyclopropyl-, 2-methyl-cyclopropyl-, cyclobutyl, cyclopentyl and cyclohexyl.

Halocycloalkyl groups are cycloalkyl groups which are substituted with one or more of the same of different halogen atoms and may optionally be substituted by one or more methyl groups. Examples of monocyclic halocycloalkyl groups are 2,2-dichloro-cyclopropyl-, 2,2-dichloro-1-methyl-cyclopropyl- and 2-chloro-4-fluoro-cyclohexyl-.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine. Examples of bicyclic groups are benzothiophenyl, benzimidazolyl, benzothiadiazolyl, quinolinyl, cinnolinyl and quinoxalinyl.

The term "heterocyclyl" is defined to include heteroaryl and in addition their unsaturated or partially unsaturated analogues such as piperidinyl, 1,3-dioxolanyl, 1,3-dioxanyl, tetrahydrofuranyl and morpholinyl.

Preferred values of $A^1$, $A^2$, $A^3$, $A^4$, X, $R^1$, $R^2$, $R^5$, $G^1$, $G^2$, $Q^1$, $Q^2$, $Y^1$, $Y^2$, $Y^3$ and $Y^4$ are, in any combination, as set out below.

Preferably $A^1$ is C—X.
Preferably $A^2$ is C—X.
Preferably $A^3$ is C—X.
Preferably $A^4$ is C—X.

Preferably each X is independently hydrogen, halogen, cyano, methyl, trifluoromethyl or methoxy, more preferably each X is independently hydrogen, fluoro, cyano, trifluoromethyl or methoxy, even more preferably each X is hydrogen, fluoro or cyano, yet even more preferably each X is hydrogen or fluoro, most preferably each X is hydrogen.

Preferably $R^1$ is hydrogen, methyl, ethyl or acetyl, more preferably hydrogen, methyl or ethyl, even more preferably hydrogen or methyl, most preferably hydrogen.

Preferably $R^2$ is hydrogen, methyl, ethyl or acetyl, more preferably hydrogen, methyl or ethyl, even more preferably hydrogen or methyl, most preferably hydrogen.

Preferably $R^5$ is trifluoromethyl.
Preferably $G^1$ is oxygen.
Preferably $G^2$ is oxygen.

Preferably $Q^1$ is aryl or aryl substituted by one to five substituents $R^3$, which may be the same or different, or $Q^1$ is heteroaryl or heteroaryl substituted by one to five substituents $R^3$, which may be the same or different, more preferably phenyl, pyridyl, furanyl, thiophenyl, pyrazolyl or 1,2,3-thiadiazolyl, or phenyl, pyridyl, furanyl, thiophenyl, pyrazolyl or 1,2,3-thiadiazolyl substituted by one to four substituents independently selected from cyano, nitro, hydroxy, bromo, chloro, fluoro, methyl, trifluoromethyl, methoxy, trifluoromethoxy, methylthio, methylsulfinyl, methylsulfonyl or phenyl, even more preferably phenyl or pyridyl, or phenyl or pyridyl substituted by one to three substituents independently selected from cyano, nitro, hydroxy, bromo, chloro, fluoro, methyl, trifluoromethyl, methoxy, trifluoromethoxy, methylthio, methylsulfinyl, methylsulfonyl or phenyl, most preferably phenyl or pyridyl substituted by one or two substituents independently selected from chloro, fluoro or methyl.

Preferably $Q^2$ is aryl or aryl substituted by one to five substituents $R^4$, which may be the same or different, or $Q^2$ is heteroaryl or heteroaryl substituted by one to five substituents $R^4$, which may be the same or different, more preferably $Q^2$ is phenyl or pyridyl, or phenyl or pyridyl substituted by one to three substituents independently selected from hydroxy, bromo, chloro, fluoro, methyl, trifluoromethyl or methoxy, even more preferably $Q^2$ is phenyl or pyridyl, or phenyl or pyridyl substituted by one or two substituents independently selected from chloro, fluoro, methyl, trifluoromethyl or methoxy.

Preferably $Y^1$ is halogen, cyano, methyl, ethyl, methoxymethyl or trifluoromethyl, more preferably bromo, chloro, cyano, methyl, ethyl, methoxymethyl or trifluoromethyl, even more preferably bromo, methyl or ethyl, yet even more preferably methyl or ethyl, most preferably methyl.

Preferably $Y^2$ is hydrogen, fluoro, chloro or methyl, most preferably hydrogen.

Preferably $Y^3$ is hydrogen, fluoro, chloro or methyl, most preferably hydrogen.

Preferably $Y^4$ is halogen, cyano, methyl, ethyl or trifluoromethyl, more preferably bromo, chloro, cyano, methyl, ethyl or trifluoromethyl, even more preferably bromo, methyl or ethyl, yet even more preferably methyl or ethyl, most preferably methyl.

A preferred embodiment are compounds of formula (Ia) wherein $A^1$, $A^2$, $A^3$, $A^4$ are CH.

A preferred embodiment are compounds of formula (Ib) wherein $A^1$ is C—F, and $A^2$, $A^3$, and $A^4$ are CH.

A preferred embodiment are compounds of formula (Ic) wherein $A^2$ is C—F, and $A^1$, $A^3$, and $A^4$ are CH.

A preferred embodiment are compounds of formula (Id) wherein $A^3$ is C—F, and $A^1$, $A^2$, and $A^4$ are CH.

A preferred embodiment are compounds of formula (Ie) wherein $A^4$ is C—F, and $A^1$, $A^2$, and $A^3$ are CH.

A preferred embodiment are compounds of formula (If) wherein $A^1$ is C—CN, and $A^2$, $A^3$, and $A^4$ are CH.

Certain intermediates are novel and as such form a further aspect of the invention. One such group of novel intermediates are compounds of formula (II')

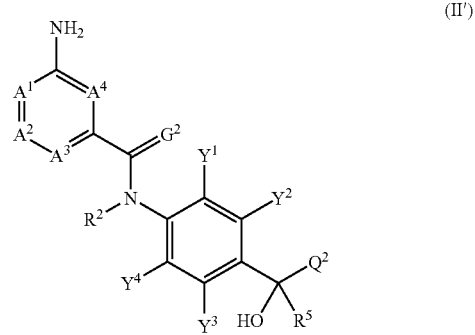

(II')

wherein $A^1$, $A^2$, $A^3$, $A^4$, $R^2$, $R^5$, $G^2$, $Q^2$, $Y^1$, $Y^2$, $Y^3$ and $Y^4$ are as defined in relation to formula (I); or a salt or N-oxide thereof. The preferences for $A^1$, $A^2$, $A^3$, $A^4$, X, $R^2$, $R^5$, $G^2$, $Q^2$, $Y^1$, $Y^2$, $Y^3$ and $Y^4$ are the same as the preferences set out for the corresponding substituents of the compounds of the formula (I).

A further group of novel intermediates are compounds of formula (IV)

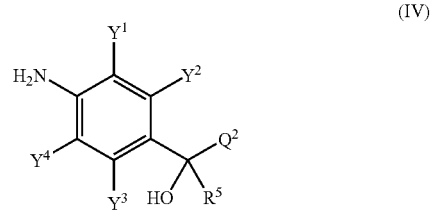

(IV)

wherein $R^5$, $Q^2$, $Y^1$, $Y^2$, $Y^3$ and $Y^4$ are as defined in relation to formula (I); or a salt or N-oxide thereof. The preferences for $R^5, Q^2, Y^1, Y^2, Y^3$ and $Y^4$ are the same as the preferences set out for the corresponding substituents of the compounds of the formula (I).

A further group of novel intermediates are compounds of formula (V)

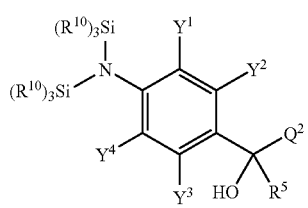

wherein $R^{10}$ is $C_1$-$C_6$alkyl, and $R^5, Q^2, Y^1, Y^2, Y^3$ and $Y^4$ are as defined in relation to formula (I); or a salt or N-oxide thereof. Preferably $R^{10}$ is methyl. The preferences for $R^5, Q^2, Y^1, Y^2, Y^3$ and $Y^4$ are the same as the preferences set out for the corresponding substituents of the compounds of the formula (I).

The compounds in Table 1 and Groups 2 to 48 below illustrate the compounds of the invention.

TABLE 1

Table 1 provides 40 compounds of formula (Ia), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-methoxy-phenyl-, and $Q^1$ has the values listed below.

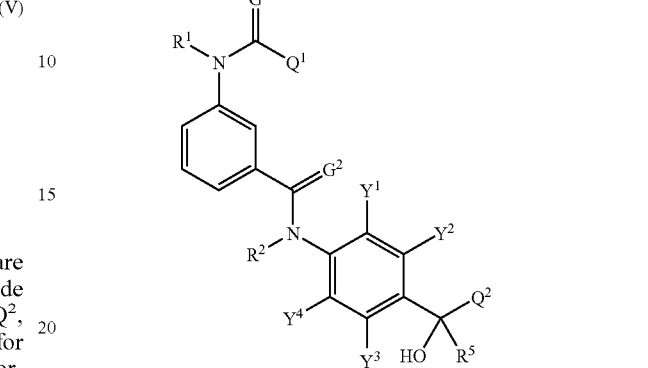

| Compound numbers | $Q^1$ |
|---|---|
| 1.01 | 5-bromo-furan-2-yl |
| 1.02 | 2-bromo-phenyl |
| 1.03 | 5-bromo-pyrid-3-yl |
| 1.04 | 2-chloro-4-fluoro-phenyl |
| 1.05 | 3-chloro-2-fluoro-phenyl, |
| 1.06 | 5-chloro-2-fluoro-phenyl |
| 1.07 | 3-chloro-2-methyl-phenyl |
| 1.08 | 2-chloro-4-nitro-phenyl |
| 1.09 | 2-chloro-5-nitro-phenyl |
| 1.10 | 2-chloro-phenyl |
| 1.11 | 3-chloro-phenyl |
| 1.12 | 2-chloro-pyrid-3-yl |
| 1.13 | 2-chloro-pyrid-4-yl |
| 1.14 | 6-chloro-pyrid-3-yl |
| 1.15 | 5-chloro-thiophen-2-yl |
| 1.16 | 3-chloro-5-trifluoromethyl-pyrid-2-yl |
| 1.17 | 4-cyano-2-fluoro-phenyl, |
| 1.18 | 4-cyano-phenyl |
| 1.19 | 2,5-dichloro-phenyl |
| 1.20 | 2,3-difluoro-phenyl |
| 1.21 | 1,3-dimethyl-1H-pyrazol-5-yl |
| 1.22 | 2-fluoro-phenyl |
| 1.23 | 4-fluoro-phenyl |
| 1.24 | 2-fluoro-pyrid-3-yl |
| 1.25 | 2-fluoro-3-trifluoromethyl-phenyl |
| 1.26 | 2-fluoro-5-trifluoromethyl-phenyl |
| 1.27 | 4-fluoro-3-trifluoromethyl-phenyl |
| 1.28 | furan-2-yl |
| 1.29 | 2-methoxy-phenyl |
| 1.30 | 2-methyl-phenyl |
| 1.31 | 3-methyl-pyrid-2-yl |
| 1.32 | 4-methyl-1,2,3-thiadiazol-5-yl |
| 1.33 | 4-nitro-phenyl |
| 1.34 | phenyl |
| 1.35 | 1,2,3-thiadiazol-4-yl |
| 1.36 | thiophen-2-yl |
| 1.37 | 2-trifluoromethoxy-phenyl |
| 1.38 | 4-trifluoromethoxy-phenyl |
| 1.39 | 2-trifluoromethyl-phenyl |
| 1.40 | 4-trifluoromethyl-phenyl |

Group 2:
Group 2 provides 40 compounds of formula (Ia), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-trifluoromethyl-phenyl-, and $Q^1$ has the values listed in Table 1.

Group 3:
Group 3 provides 40 compounds of formula (Ia), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-chloro-phenyl-, and $Q^1$ has the values listed in Table 1.

Group 4:
Group 4 provides 40 compounds of formula (Ia), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-fluoro-phenyl-, and $Q^1$ has the values listed in Table 1.

Group 5:
Group 5 provides 40 compounds of formula (Ia), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3-fluoro-phenyl-, and $Q^1$ has the values listed in Table 1.

Group 6:
Group 6 provides 40 compounds of formula (Ia), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is phenyl-, and $Q^1$ has the values listed in Table 1.

Group 7:
Group 7 provides 40 compounds of formula (Ia), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3,5-dichloro-phenyl-, and $Q^1$ has the values listed in Table 1.

Group 8:
Group 8 provides 40 compounds of formula (Ia), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are bromo, $Q^2$ is 3,5-dichloro-phenyl-, and $Q^1$ has the values listed in Table 1.

Group 9:
Group 9 provides 40 compounds of formula (Ib), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-methoxy-phenyl-, and $Q^1$ has the values listed in Table 1.

(Ib)

Group 10:
Group 10 provides 40 compounds of formula (Ib), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-trifluoromethyl-phenyl-, and $Q^1$ has the values listed in Table 1.

Group 11:
Group 11 provides 40 compounds of formula (Ib), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-chloro-phenyl-, and $Q^1$ has the values listed in Table 1.

Group 12:
Group 12 provides 40 compounds of formula (Ib), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-fluoro-phenyl-, and $Q^1$ has the values listed in Table 1.

Group 13:
Group 13 provides 40 compounds of formula (Ib), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3-fluoro-phenyl-, and $Q^1$ has the values listed in Table 1.

Group 14:
Group 14 provides 40 compounds of formula (Ib), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is phenyl-, and $Q^1$ has the values listed in Table 1.

Group 15:
Group 15 provides 40 compounds of formula (Ib), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3,5-dichloro-phenyl-, and $Q^1$ has the values listed in Table 1.

Group 16:
Group 16 provides 40 compounds of formula (Ib), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are bromo, $Q^2$ is 3,5-dichloro-phenyl-, and $Q^1$ has the values listed in Table 1.

Group 17:
Group 17 provides 40 compounds of formula (Ic), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-methoxy-phenyl-, and $Q^1$ has the values listed in Table 1.

(Ic)

Group 18:
Group 18 provides 40 compounds of formula (Ic), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-trifluoromethyl-phenyl-, and $Q^1$ has the values listed in Table 1.

Group 19:
Group 19 provides 40 compounds of formula (Ic), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-chloro-phenyl-, and $Q^1$ has the values listed in Table 1.

Group 20:
Group 20 provides 40 compounds of formula (Ic), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-fluoro-phenyl-, and $Q^1$ has the values listed in Table 1.

Group 21:
Group 21 provides 40 compounds of formula (Ic), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3-fluoro-phenyl-, and $Q^1$ has the values listed in Table 1.

Group 22:
Group 22 provides 40 compounds of formula (Ic), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is phenyl-, and $Q^1$ has the values listed in Table 1.

Group 23:
Group 23 provides 40 compounds of formula (Ic), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3,5-dichloro-phenyl-, and $Q^1$ has the values listed in Table 1.

Group 24:
Group 24 provides 40 compounds of formula (Ic), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are bromo, $Q^2$ is 3,5-dichloro-phenyl-, and $Q^1$ has the values listed in Table 1.

Group 25:
Group 25 provides 40 compounds of formula (Id), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-methoxy-phenyl-, and $Q^1$ has the values listed in Table 1.

(Id)

Group 26:
Group 26 provides 40 compounds of formula (Id), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-trifluoromethyl-phenyl-, and $Q^1$ has the values listed in Table 1.

Group 27:
Group 27 provides 40 compounds of formula (Id), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-chloro-phenyl-, and $Q^1$ has the values listed in Table 1.

Group 28:
Group 28 provides 40 compounds of formula (Id), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-fluoro-phenyl-, and $Q^1$ has the values listed in Table 1.

Group 29:
Group 29 provides 40 compounds of formula (Id), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3-fluoro-phenyl-, and $Q^1$ has the values listed in Table 1.

Group 30:
Group 30 provides 40 compounds of formula (Id), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is phenyl-, and $Q^1$ has the values listed in Table 1.

Group 31:
Group 31 provides 40 compounds of formula (Id), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3,5-dichloro-phenyl-, and $Q^1$ has the values listed in Table 1.

Group 32:
Group 32 provides 40 compounds of formula (Id), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are bromo, $Q^2$ is 3,5-dichloro-phenyl-, and $Q^1$ has the values listed in Table 1.

Group 33:
Group 33 provides 40 compounds of formula (Ie), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-methoxy-phenyl-, and $Q^1$ the values listed in Table 1.

(Ie)

Group 34:
Group 34 provides 40 compounds of formula (Ie), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-trifluoromethyl-phenyl-, and $Q^1$ has the values listed in Table 1.

Group 35:
Group 35 provides 40 compounds of formula (Ie), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-chloro-phenyl-, and $Q^1$ has the values listed in Table 1.

Group 36:
Group 36 provides 40 compounds of formula (Ie), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-fluoro-phenyl-, and $Q^1$ has the values listed in Table 1.

Group 37:
Group 37 provides 40 compounds of formula (Ie), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3-fluoro-phenyl-, and $Q^1$ has the values listed in Table 1.

Group 38:
Group 38 provides 40 compounds of formula (Ie), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is phenyl-, and $Q^1$ has the values listed in Table 1.

Group 39:
Group 39 provides 40 compounds of formula (Ie), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3,5-dichloro-phenyl-, and $Q^1$ has the values listed in Table 1.

Group 40:
Group 40 provides 40 compounds of formula (Ie), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are bromo, $Q^2$ is 3,5-dichloro-phenyl-, and $Q^1$ has the values listed in Table 1.

Group 41:
Group 41 provides 40 compounds of formula (If), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-methoxy-phenyl-, and $Q^1$ the values listed in Table 1.

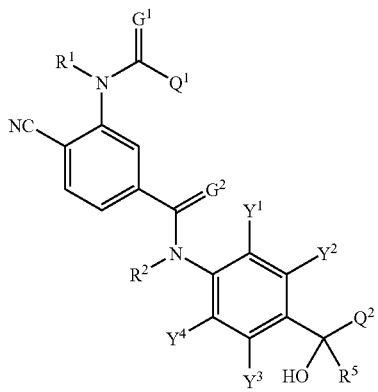

(If)

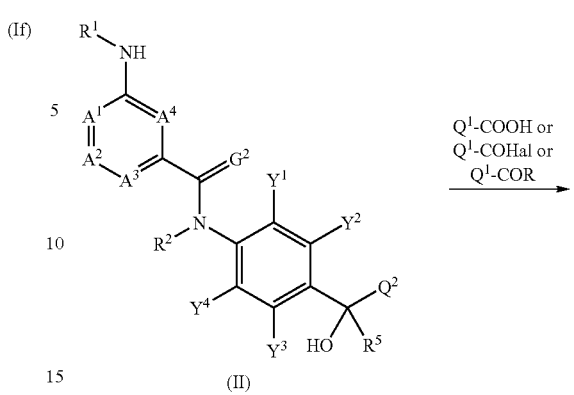

Group 42:

Group 42 provides 40 compounds of formula (If), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-trifluoromethyl-phenyl-, and $Q^1$ has the values listed in Table 1.

Group 43:

Group 43 provides 40 compounds of formula (If), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-chloro-phenyl-, and $Q^1$ has the values listed in Table 1.

Group 44:

Group 44 provides 40 compounds of formula (If), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 4-fluoro-phenyl-, and $Q^1$ has the values listed in Table 1.

Group 45:

Group 45 provides 40 compounds of formula (If), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3-fluoro-phenyl-, and $Q^1$ has the values listed in Table 1.

Group 46:

Group 46 provides 40 compounds of formula (If), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is phenyl-, and $Q^1$ has the values listed in Table 1.

Group 47:

Group 47 provides 40 compounds of formula (If), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are methyl, $Q^2$ is 3,5-dichloro-phenyl-, and $Q^1$ has the values listed in Table 1.

Group 48:

Group 48 provides 40 compounds of formula (If), wherein $R^1$ and $R^2$ are hydrogen, $R^5$ is trifluoromethyl, $G^1$ and $G^2$ are oxygen, $Y^2$ and $Y^3$ are hydrogen, $Y^1$ and $Y^4$ are bromo, $Q^2$ is 3,5-dichloro-phenyl-, and $Q^1$ has the values listed in Table 1.

The compounds of the invention may be made by a variety of methods.

1) Compounds of formula (I), wherein $G^1$ and $G^2$ are oxygen, may be made by the treatment of a compound of formula (II), wherein $G^2$ is oxygen, with a carboxylic acid of formula $Q^1$-COOH, an acid halide of formula $Q^1$-COHal, wherein Hal is Cl, F or Br or an ester of formula $Q^1$-COR, wherein R is $C_1$-$C_6$alkoxy.

When a carboxylic acid is used such reactions are usually carried out in the presence of a coupling reagent, such as N,N-dicyclohexylcarbodiimide ("DCC"), 1-ethyl-3-[3-dimethylamino-propyl]carbodiimide hydrochloride ("EDC") or bis(2-oxo-3-oxazolidinyl)phosphonic chloride ("BOP-Cl"), in the presence of a base, such as pyridine, triethylamine, 4-(dimethylamino)-pyridine or diisopropylethylamine, and optionally in the presence of a nucleophilic catalyst, such as hydroxybenzotriazole. When an acid halide is used, such reactions are usually carried out under basic conditions (for example in the presence of pyridine, triethylamine, 4-(dimethylamino)-pyridine or diisopropylethylamine), again optionally in the presence of a nucleophilic catalyst. When an ester is used it is sometimes possible to convert the ester directly to the amide by heating the ester and amine together in a thermal process.

2a) Compounds of formula (IIa), wherein $G^2$ is oxygen, may be made by treatment of an amine of formula (IV) with an acid chloride of formula (III), wherein $G^2$ is oxygen, under basic conditions (for example in the presence of an organic base such as pyridine, triethylamine, 4-(dimethylamino)-pyridine, diisopropylethylamine, or an excess of the amine $HNR^2Q^2$ or in the presence of an acid scavenger such as sodium carbonate, sodium hydrogen carbonate, potassium carbonate or potassium hydrogen carbonate). The reaction can preferably be carried out in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof.

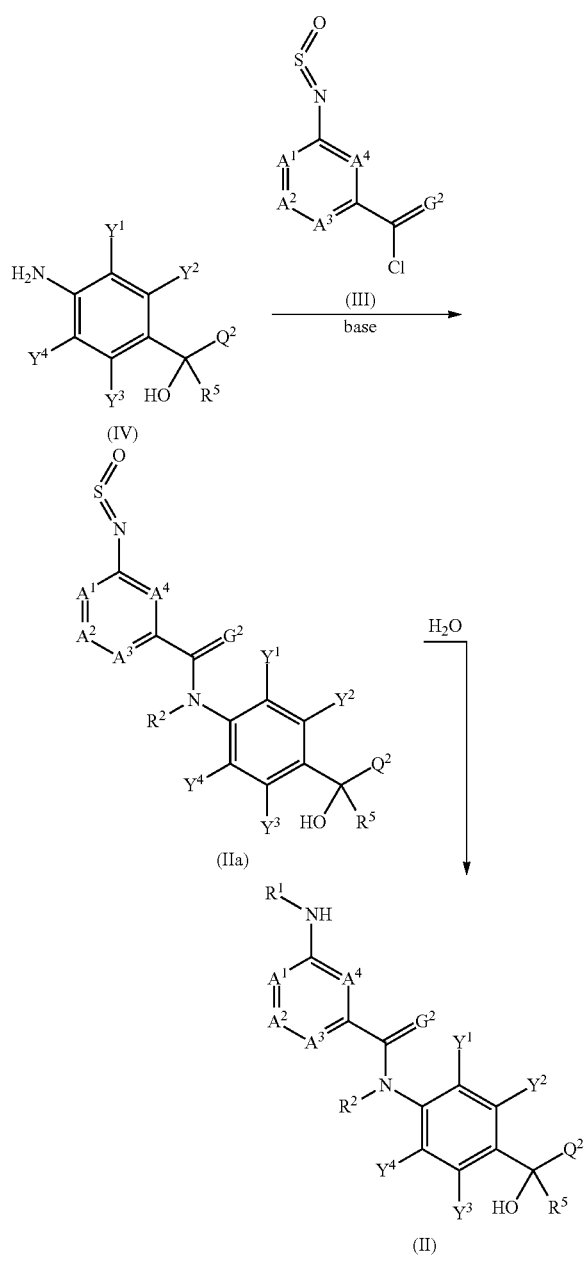

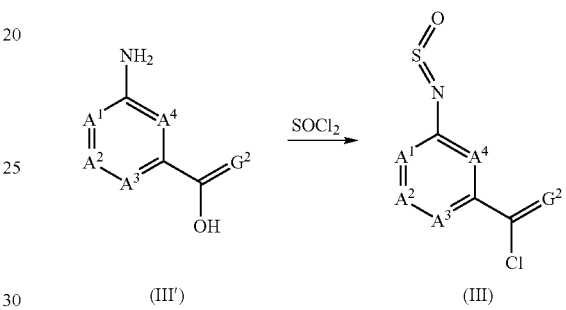

them into compounds of formula (II), which are usually easier to handle. Furthermore, this reduces the number of practical steps by one, as the last transformation can conveniently be achieved during the aqueous work-up of the reaction mixture to compounds of formula (IIa). The reaction can preferably be carried out in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof.

3) Acid chlorides of formula (III) may be made from an amino-carboxylic acid of formula (III') by methods known to a person skilled in the art, such as treatment with thionyl chloride. This reaction is described, for example, in Journal fuer Praktische Chemie (Leipzig) (1937), 148, 161-9.

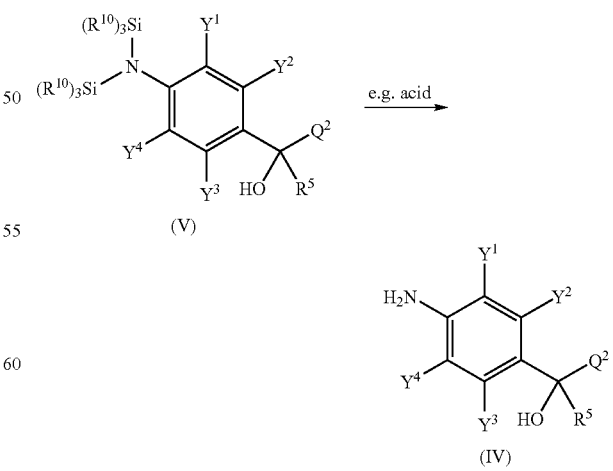

The reaction can preferably be carried on in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof.

4) Compounds of formula (IV), may be made by treatment of a compound of formula (V), wherein $R^{10}$ is $C_1$-$C_6$alkyl, with concentrated acid, such as hydrochloric acid, optionally in the presence of a diluent, such as tetrahydrofuran, or by treatment with a source of fluoride ion, such as tetrabutylammonium fluoride.

2b) Compounds of formula (II), wherein $G^2$ is oxygen and $R^1$ is hydrogen, may be made by treatment of a compound of formula (IIa) with water under neutral or acidic or basic conditions (preferably acidic conditions, for example in the presence of dilute aqueous hydrochloric acid). The reaction can preferably be carried out in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof (such as a mixture of dichloromethane and tetrahydrofuran).

2c) Alternatively, compounds of formula (II), wherein $G^2$ is oxygen and $R^1$ is hydrogen, may be made by combination of a reaction of type 2a) with a reaction of type 2b). As compounds of formula (IIa) can be sensitive towards hydrolysis, it is convenient not to isolate them but to directly transform The reaction can preferably be carried on in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof.

5) Compounds of formula (V), wherein $R^{10}$ is $C_1$-$C_6$alkyl, may be made by treatment of a compound of formula (VI), wherein $R^{10}$ is $C_1$-$C_6$alkyl, with a base, such as n-butyl lithium, in the presence of a diluent, such as tetrahydrofuran, followed by addition of a ketone of formula $R^5$—C(O)-$Q^2$. A similar preparation is described, for example, in Bioorganic & Medicinal Chemistry (2004), 12(5), 979-993.

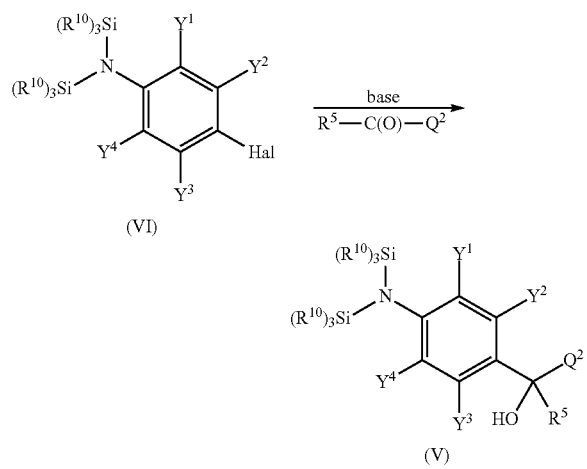

Ketones of formula $R^5$—C(O)-$Q^2$ are either known compounds or may be made by methods known to a person skilled in the art. Many ketones of formula $R^5$—C(O)-$Q^2$ are commercially available.

6) Compounds of formula (VI), wherein $R^{10}$ is $C_1$-$C_6$alkyl, may be made by treatment of a compound of formula (VII), with a base, such as n-butyl lithium, in the presence of a diluent, such as tetrahydrofuran, followed by addition of a silyl halide of formula $(R^{10})_3$Si-Hal, such as trimethylsilyl chloride. The sequence is repeated to introduce the second silyl group. A similar preparation is described, for example, in Journal of Organometallic Chemistry (1979), 164(1), 11-18.

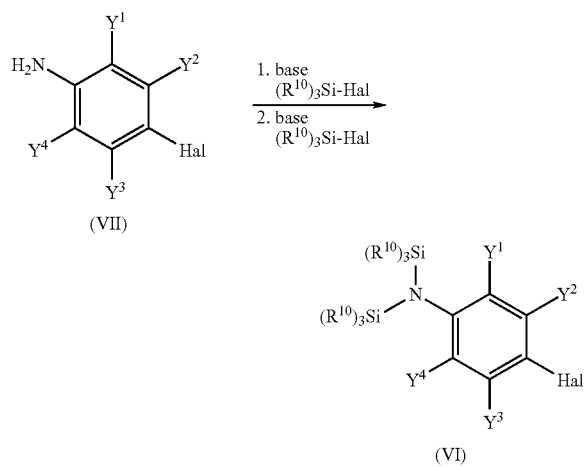

Compounds of formula (VII) are either known compounds or may be made by methods known to a person skilled in the art, like the ring halogenation of the corresponding aniline. Many compounds of formula (VII) are commercially available.

7) Compounds of formula (I), wherein $G^1$ and $G^2$ are sulfur, may be made from a compound of formula (I), wherein $G^1$ and $G^2$ are oxygen, by treatment with a thio-transfer reagent, such as Lawesson's reagent or phosphorus pentasulfide.

8) Compounds of formula (I), wherein $G^1$ is sulfur and $G^2$ is oxygen, may be made from a compound of formula (II), wherein $G^2$ is oxygen, and coupling with a thio analogue such as a thiocarboxylic acid of formula $Q^1$-CSOH or a thioacid halide of formula $Q^1$-CSHal, wherein Hal is Cl, F or Br.

9) Compounds of formula (I), wherein $G^1$ is oxygen and $G^2$ is sulfur, may be made from a compound of formula (II) which is treated with a thio-transfer reagent, such as Lawessen's reagent or phosphorus pentasulfide, prior to coupling with a carboxylic acid of formula $Q^1$-COOH, an acid halide of formula $Q^1$-COHal, wherein Hal is Cl, F or Br or an ester of formula $Q^1$-COR, wherein R is $C_1$-$C_6$alkoxy.

10) Compounds of formula (II) wherein X is cyano, can be made from a compound of formula (II*) wherein LG is halogen, such as bromide or iodide, by reaction with a cyanide salt, such as copper cyanide or zinc cyanide in presence of a palladium catalyst.

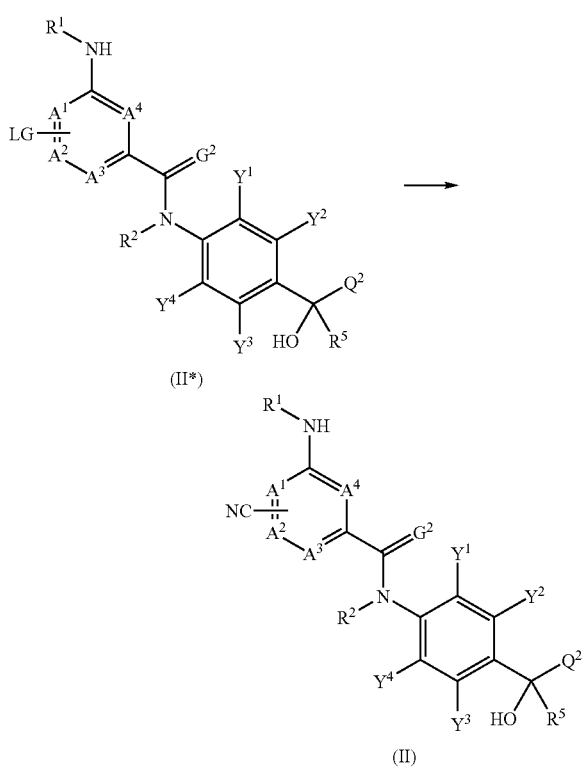

Similar reactions with copper cyanide have been described in, for example, J. Med. Chem. (2004), 47(8), 1969-1986, J. Med. Chem. (2002), 45(17), 3692-3702 and J. Med. Chem. (1989), 32(3), 575-83. Similar reactions with zinc cyanide in the presence of a palladium catalyst have been described in, for example, Bioorganic & Medicinal Chemistry Letters (2007), 17(7), 1908. The displacement of a halogen with cyanide can also be carried out on compounds of formula (I) and (III).

11) Compounds of formula (II) wherein X is cyano, can be made from a compound of formula (II') wherein LG is an amine, by reaction with a cyanide salt, such as copper cyanide, via a diazotization reaction.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus*, and *R. santonensis*) and the *Termitidae* (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;
q) Pymetrozine;
r) Spirotetramat, spirodiclofen or spiromesifen; or
s) Flubendiamid or rynaxypyr In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N-([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

Example I1

Preparation of 2-(4-bromo-2,6-dimethyl-phenyl)-1,1,1,3,3,3-hexamethyl-disilazane

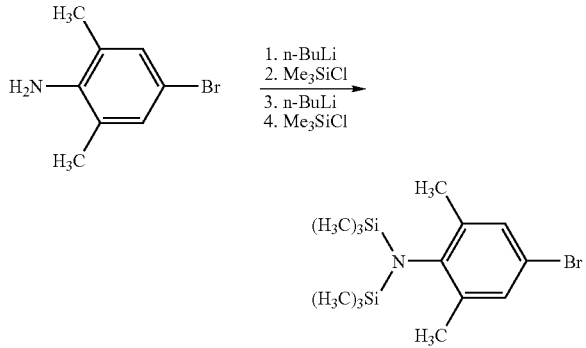

To a solution of 4-bromo-2,6-dimethylaniline (commercially available) (40 g, 0.2 mol) in tetrahydrofuran (500 ml) under a nitrogen atmosphere was added a solution of n-butyl lithium in hexanes (1.6 M) (125 ml, 0.2 mol). During this operation, the internal temperature was kept between −70° C. and −78° C. After five minutes, trimethylsilyl chloride (25 ml, 0.2 mol) was added whilst the internal temperature was kept below −68° C. After five minutes, the cooling bath was replaced with a water bath and the internal temperature rose to 0° C. Then the cooling bath was put back and the reaction mixture was cooled to −78° C. To this solution, a solution of n-butyl lithium in hexanes (1.6 M) (125 ml, 0.2 mol) was added whilst keeping the internal temperature below −70° C., followed by addition of trimethylsilyl chloride (30 ml, 0.237 mol) whilst keeping the internal temperature below −68° C. The reaction mixture was gradually allowed to warm to 20° C. Hexanes (200 ml) and water (40 ml) were added and the phases were separated. The organic phase was washed with brine, dried over sodium sulfate, and concentrated. The residue was distilled under a high vacuum leading to the title compound as a colorless oil which crystallized on standing. M.p. 47-52° C. $^1$H-NMR (CDCl$_3$, 400 MHz): 0.08 (s, 18H), 2.21 (s, 6H), 7.15 (s, 2H) ppm.

Example I2

Preparation of 2,2,2-trifluoro-1-(4-fluoro-phenyl)-1-[4-(1,1,1,3,3,3-hexamethyl-disilazan-2-yl)-3,5-dimethyl-phenyl]-ethanol (Compound D4 of Table D)

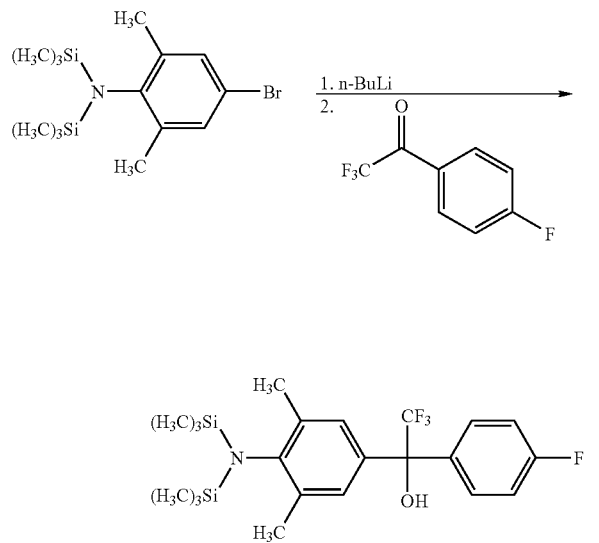

To a solution of 2-(4-bromo-2,6-dimethyl-phenyl)-1,1,1,3,3,3-hexamethyl-disilazane (Example I1) (1.72 g, 5.0 mmol) in tetrahydrofuran (12 ml) under a nitrogen atmosphere was slowly added a solution of n-butyl lithium in hexanes (1.6 M) (3.3 ml, 5.28 mmol) at −70° C. The reaction mixture was stirred at −70° C. for 30 minutes before addition of 2,2,2,4'-tetrafluoroacetophenone (commercially available) (1.01 g, 5.25 mmol) at −70° C. The cooling bath was removed after 15 minutes. Once the reaction mixture had reached ambient temperature, it was poured onto water. The mixture was extracted with diethyl ether. The organic phase was washed with water and brine, dried over sodium sulfate, and then concentrated. The title compound was isolated as a yellow oil.

The same method was used with 4'-methoxy-2,2,2-trifluoroacetophenone as reagent to yield Compound D1 of Table D, with 4'-trifluoromethyl-2,2,2-trifluoroacetophenone as reagent to yield Compound D2 of Table D, with 4'-chloro-2,2,2-trifluoroacetophenone as reagent to yield Compound D3 of Table D, with 2,2,2,3'-tetrafluoroacetophenone as reagent to yield Compound D5 of Table D, and with 2,2,2-trifluoroacetophenone as reagent to yield Compound D6 of Table D.

Example I3

Preparation of 1-(4-amino-3,5-dimethyl-phenyl)-2,2,2-trifluoro-1-(4-fluorophenyl)-ethanol (Compound C4 of Table C)

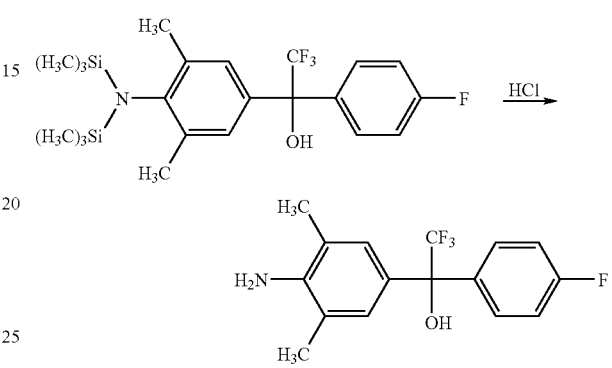

To a solution of 2,2,2-trifluoro-1-(4-fluoro-phenyl)-1-[4-(1,1,1,3,3,3-hexamethyl disilazan-2-yl)-3,5-dimethyl-phenyl]-ethanol (Example I2) (5 mmol) in tetrahydrofuran (15 ml) was added aqueous hydrochloric acid (concentrated) (1 ml) at 20° C. The reaction mixture was stirred at 20° C. for 15 hours. The reaction mixture was neutralized by addition of aqueous sodium hydroxide (4M). The mixture was extracted with diethyl ether. The organic phase was dried over sodium sulfate, filtered through a plug of silica gel and concentrated. The residue was triturated with heptane and a small amount of diethyl ether, then filtered and dried. The title compound was isolated as off-white crystals.

The same method was used to give Compound C1 of Table C, Compound C2 of Table C, Compound C3 of Table C, Compound C5 of Table C, and Compound C6 of Table C.

Example I4

Preparation of 3-amino-N-{2,6-dimethyl-4-[2,2,2-trifluoro-1-(4-fluoro-phenyl)-1-hydroxy-ethyl]-phenyl}-benzamide (Compound B4 of Table B)

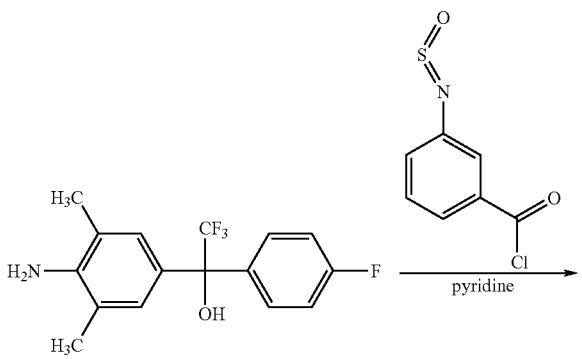

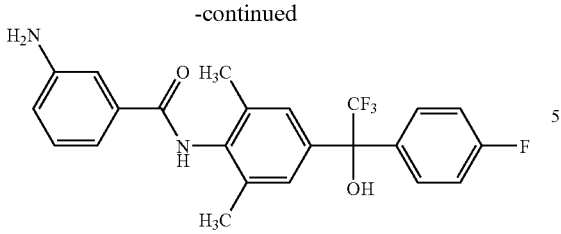

To a solution of 1-(4-amino-3,5-dimethyl-phenyl)-2,2,2-trifluoro-1-(4-fluorophenyl)-ethanol (Example I3) (0.313 g, 1.0 mmol) in absolute dichloromethane (10 ml), at 20° C., was added sequentially a solution of 3-sulfinylamino-benzoyl chloride (0.201 g, 1.0 mmol) (the 3-sulfinylamino-benzoyl chloride was prepared in situ by refluxing 3-amino-benzoic acid in thionyl chloride) in absolute dichloromethane (1 ml) and a solution of pyridine (0.087 g, 1.1 mmol) in absolute dichloromethane (1 ml). After one hour, the reaction mixture was quenched by addition of water (0.5 ml) and aqueous hydrochloric acid (1M) (1 ml). After separation of the phases, the aqueous layer was extracted with dichloromethane. The combined organic phases were dried over sodium sulfate and concentrated. The residue was purified by column chromatography over silica gel (eluent: ethyl acetate/hexanes 1:3 to 1:1). The title compound was isolated as colorless crystals.

The same method was used to give Compound B1 of Table B, Compound B2 of Table B, Compound B3 of Table B, Compound B5 of Table B, and Compound B6 of Table B.

Example I5

Preparation of 1-(4-amino-3,5-dibromo-phenyl)-2,2,2-trifluoro-ethanone

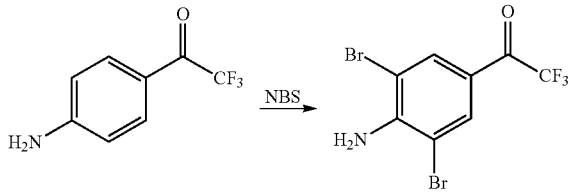

To a solution of 4-trifluoroacetylaniline (commercially available) (0.378 g, 2.0 mmol) in dichloromethane was added N-bromosuccinimide ("NBS") (0.743 g, 4.20 mmol). The reaction mixture was stirred at ambient temperature for 16 hours. The reaction mixture was poured onto a mixture of aqueous sodium hydroxide (1N) (50 ml) and ethyl acetate (50 ml). The phases were separated and the aqueous phase extracted three times with ethyl acetate (50 ml). The combined organic extracts were dried over sodium sulfate and concentrated. The residue was purified by column chromatography on silica gel (eluent: cyclohexane/ethyl acetate 3:1 to 0:1) to give the title compound. $^1$H-NMR (400 MHz, CDCl$_3$): 8.12 (2H, s), 5.40 (2H, s).

Example I6

Preparation of 1-(amino-3,5-dibromo-phenyl)-1-(3,5-dichloro-phenyl)-2,2,2-trifluoro-ethanol (Compound C7 of Table C)

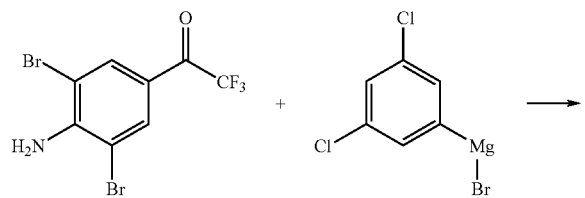

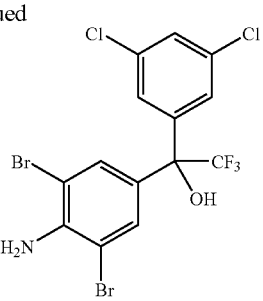

To a solution of 1-(4-amino-3,5-dibromo-phenyl)-2,2,2-trifluoro-ethanone (Example I5) (0.250 g, 0.72 mmol) in tetrahydrofuran (15 ml) was added (3,5-dichloro-phenyl) magnesium bromide (commercially available) (0.5 N) (5.76 ml, 2.88 mmol) at 0° C. The reaction mixture was stirred at 0° C. for 4 hours. The reaction mixture was quenched by addition of aqueous ammonium chloride (saturated) and extracted three times with ethyl acetate (50 ml). The combined organic extracts were dried over sodium sulfate and concentrated. The residue was suspended in chloroform and precipitated with cyclohexane. The solid was isolated via filtration and washed with cyclohexane to give the title compound. $^1$H-NMR (400 MHz, CDCl$_3$): 7.45 (2H, s), 7.37 (3H, s), 4.72 (2H, s), 2.9 (1H, s).

Example I7

Preparation of N-{2,6-bibromo-4-[1-(3,5-dichloro-phenyl)-2,2,2-trifluoro-1-hydroxy-ethyl]-phenyl}-3-nitro-benzamide

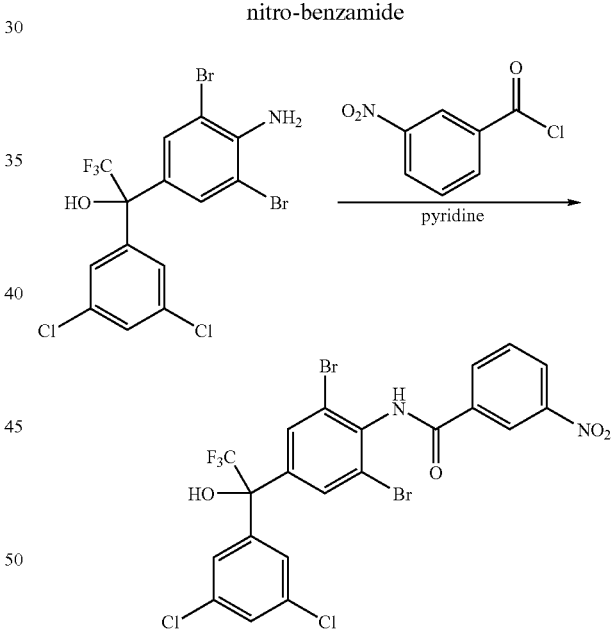

To a solution of 1-(4-amino-3,5-dibromo-phenyl)-1-(3,5-dichloro-phenyl)-2,2,2-trifluoro-ethanol (Example I7) (0.242 mg, 0.49 mmol) in tetrahydrofuran (5 ml) were added successively pyridine (0.158 ml, 1.96 mmol) and 3-nitrobenzoyl chloride (0.182 g, 0.98 mmol). The reaction mixture was stirred at 90° C. in a sealed vial for 24 hours. The reaction mixture was allowed to cool to ambient temperature and then quenched by addition of aqueous sodium hydrogen carbonate (saturated). The phases were separated and the aqueous phase was extracted three times with ethyl acetate. The combined organic extracts were dried over sodium sulfate and concentrated. The residue was purified by column chromatography on silica gel (eluent: cyclohexane/ethyl acetate 4:1) to give the title compound. $^1$H-NMR (400 MHz, CHCl$_3$): 8.79 (s, 1H), 8.48 (d, 1H), 8.31 (d, 1H), 7.76 (m, 3H), 7.41 (m, 3H) ppm.

Example I8

Preparation of 3-amino-N-{2,6-dibromo-4-[1-(3,5-dichloro-phenyl)-2,2,2-trifluoro-1-hydroxy-ethyl]-phenyl}-benzamide (Compound B7 of Table B)

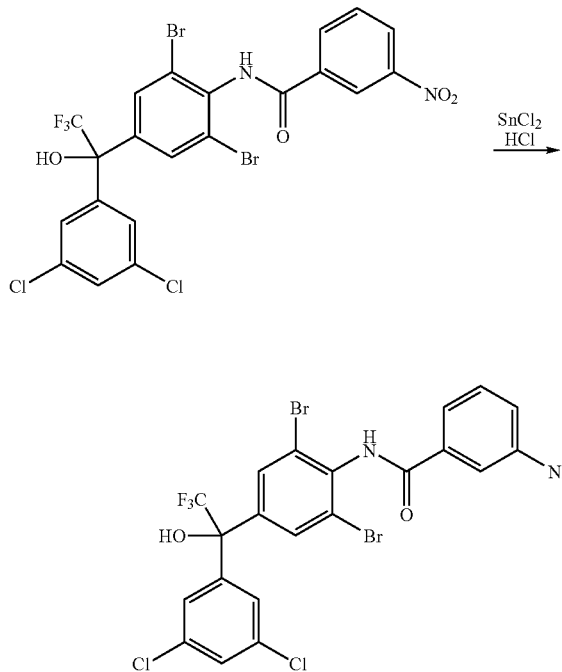

To a solution of N-{2,6-dibromo-4-[1-(3,5-dichloro-phenyl)-2,2,2-trifluoro-1-hydroxy-ethyl]-phenyl}-3-nitro-benzamide (Example I7) (0.206 g, 0.32 mmol) in isopropanol (15 ml) was added tin(II) chloride (0.218 g, 1.15 mmol). The mixture was cooled to 0° C. and aqueous hydrochloric acid (concentrated) (0.263 ml) was added slowly. The reaction mixture was stirred at 80° C. for 0.5 hours. ⅓ of the total volume of isopropanol was evaporated. Water (100 ml) was added to the concentrated mixture and aqueous sodium hydroxide (5N) was added to adjust the pH to 9. The aqueous phase was extracted three times with ethyl acetate (3×50 ml). The combined organic extracts were washed with water and brine, dried over sodium sulfate, and then concentrated. The residue was used without further purification. $^1$H-NMR (400 MHz, CDCl$_3$): 8.22 (s, 1H), 7.72 (m, 3H), 7.47 (s, 2H), 7.12 (m, 3H), 6.77 (d, 1H), 5.35 (s, 2H) ppm.

Example P1

Preparation of 3-benzoylamino-N-{2,6-dimethyl-4-[2,2,2-trifluoro-1-(4-fluoro-phenyl)-1-hydroxy-ethyl]-phenyl}-benzamide (Compound A20 of Table A)

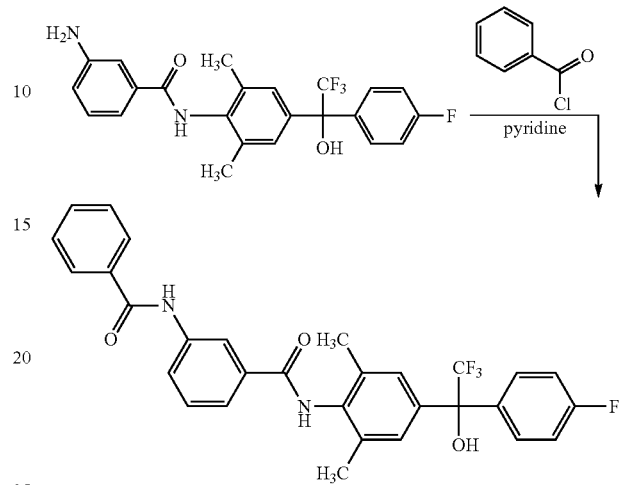

To a solution of 3-amino-N-{2,6-dimethyl-4-[2,2,2-trifluoro-1-(4-fluoro-phenyl)-1-hydroxy-ethyl]-phenyl}-benzamide (0.064 g, 0.15 mmol) (Example I4) in absolute dichloromethane (2 ml), at 20° C., was added a solution of benzoyl chloride (0.021 g, 0.15 mmol) in dichloromethane (0.5 ml). After 10 minutes, the suspension was treated with a solution of pyridine (0.016 g, 0.2 mmol) in dichloromethane (0.5 ml). The solution was stirred at 20° C. for 2 hours. The reaction mixture was quenched by addition of water (2 ml) and a few drops of aqueous hydrochloric acid (1M). The phases were separated and the aqueous phase was extracted with dichloromethane. The organic phases were dried over sodium sulfate, filtered through a plug silica gel which was further washed with ethyl acetate and concentrated. The residue was triturated in hexanes, filtered, washed with pentane and dried to yield the title compound as colorless crystals.

The same method was used to give Compounds A1-A19 of Table A, and Compounds A21-A22 of Table A.

Example P2

Preparation of 3-[(4-cyanobenzoyl)-amino]-N-{2,6-dibromo-4-[1-(3,5-dichloro-phenyl)-2,2,2-trifluoro-1-hydroxy-ethyl]-phenyl}-benzamide (Compound A23 of Table A)

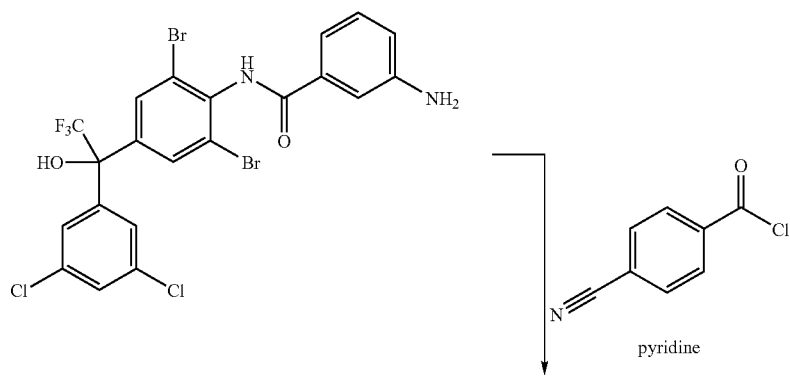

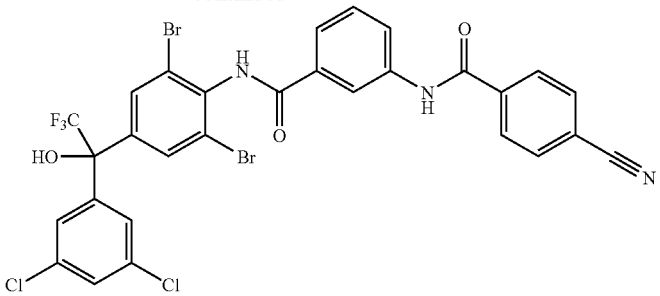

To a solution of 3-amino-N-{2,6-dibromo-4-[1-(3,5-dichloro-phenyl)-2,2,2-trifluoro-1-hydroxy-ethyl]-phenyl}-benzamide (Example I8) (0.147 mg, 0.24 mmol) in tetrahydrofuran (5 ml) were added successively pyridine (0.058 ml, 0.72 mmol) and 4-cyano-benzoyl chloride (48 mg, 0.29 mmol). The reaction mixture was stirred at ambient temperature for 2 hours. Aqueous sodium hydrogen carbonate (saturated) was added and the phases were separated. The aqueous phase was extracted twice with ethyl acetate. The combined organic extracts were dried over sodium sulfate and concentrated. The residue was purified by column chromatography on silica gel (eluent: cyclohexane/ethyl acetate 1:1) to give the title compound.

TABLE A

Compounds of formula (Ia')

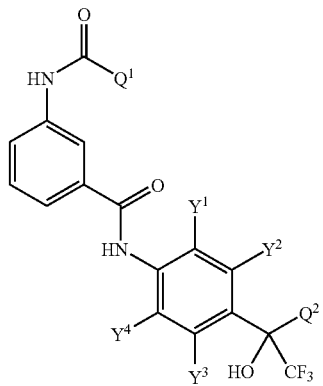

| Compound No. | $Y^1$ | $Y^2$ | $Y^3$ | $Y^4$ | $Q^1$ | $Q^2$ | M.p. (° C.) |
|---|---|---|---|---|---|---|---|
| A1 | Me | H | H | Me | 2-chloro-pyrid-4-yl- | 4-methoxy-phenyl- | 135 (decomposes) |
| A2 | Me | H | H | Me | 2-chloro-pyrid-4-yl- | 4-trifluoromethyl-phenyl- | 234-236 |
| A3 | Me | H | H | Me | 2-chloro-pyrid-4-yl- | 4-chloro-phenyl- | 237-238 |
| A4 | Me | H | H | Me | 2-chloro-pyrid-4-yl- | 4-fluoro-phenyl- | 189-192 |
| A5 | Me | H | H | Me | 2,3-difluoro-phenyl- | 4-methoxy-phenyl- | 152 (decomposes) |
| A6 | Me | H | H | Me | 2,3-difluoro-phenyl- | 4-trifluoromethyl-phenyl- | 229-230 |
| A7 | Me | H | H | Me | 2,3-difluoro-phenyl- | 4-chloro-phenyl- | 189-190 |
| A8 | Me | H | H | Me | 2,3-difluoro-phenyl- | 4-fluoro-phenyl- | 195-197 |
| A9 | Me | H | H | Me | 2,3-difluoro-phenyl- | 3-fluoro-phenyl- | 185-186 |
| A10 | Me | H | H | Me | 2,3-difluoro-phenyl- | phenyl- | 226-227 |
| A11 | Me | H | H | Me | 4-fluoro-phenyl- | 4-methoxy-phenyl- | 130 (decomposes) |
| A12 | Me | H | H | Me | 4-fluoro-phenyl- | 4-trifluoromethyl-phenyl- | >250 |
| A13 | Me | H | H | Me | 4-fluoro-phenyl- | 4-chloro-phenyl- | 220-221 |
| A14 | Me | H | H | Me | 4-fluoro-phenyl- | 4-fluoro-phenyl- | 181-184 |
| A15 | Me | H | H | Me | 4-fluoro-phenyl- | 3-fluoro-phenyl- | 165-167 |
| A16 | Me | H | H | Me | 4-fluoro-phenyl- | phenyl- | >250 |
| A17 | Me | H | H | Me | phenyl- | 4-methoxy-phenyl- | 128 (decomposes) |
| A18 | Me | H | H | Me | phenyl- | 4-trifluoromethyl-phenyl- | 225-226 |
| A19 | Me | H | H | Me | phenyl- | 4-chloro-phenyl- | 145-147 |
| A20 | Me | H | H | Me | phenyl- | 4-fluoro-phenyl- | 210-212 |
| A21 | Me | H | H | Me | phenyl- | 3-fluoro-phenyl- | 140-143 |

TABLE A-continued

Compounds of formula (Ia')

(Ia')

| Compound No. | Y¹ | Y² | Y³ | Y⁴ | Q¹ | Q² | M.p. (° C.) |
|---|---|---|---|---|---|---|---|
| A22 | Me | H | H | Me | phenyl- | phenyl- | 222-225 |
| A23 | Br | H | H | Br | 4-cyano-phenyl- | 3,5-dichloro-phenyl- | 165-168 |

TABLE B

Compounds of formula (IIa')

(IIa')

| Compound No. | Y¹ | Y² | Y³ | Y⁴ | Q² | M.p. (° C.) |
|---|---|---|---|---|---|---|
| B1 | Me | H | H | Me | 4-methoxy-phenyl- | 188-189 |
| B2 | Me | H | H | Me | 4-trifluoromethyl-phenyl- | 217-218 |
| B3 | Me | H | H | Me | 4-chloro-phenyl- | 210-212 |
| B4 | Me | H | H | Me | 4-fluoro-phenyl- | 211-212 |
| B5 | Me | H | H | Me | 3-fluoro-phenyl- | 224-226 |
| B6 | Me | H | H | Me | phenyl- | 214-215 |
| B7 | Br | H | H | Br | 3,5-dichloro-phenyl- | — |

TABLE C

Compounds of formula (IVa')

(IVa')

| Compound No. | Y¹ | Y² | Y³ | Y⁴ | Q² | M.p. (° C.) |
|---|---|---|---|---|---|---|
| C1 | Me | H | H | Me | 4-methoxy-phenyl- | 159-161 |
| C2 | Me | H | H | Me | 4-trifluoromethyl-phenyl- | 162-163 |
| C3 | Me | H | H | Me | 4-chloro-phenyl- | 177-178 |
| C4 | Me | H | H | Me | 4-fluoro-phenyl- | 141-142 |
| C5 | Me | H | H | Me | 3-fluoro-phenyl- | 154-155 |
| C6 | Me | H | H | Me | phenyl- | 162-163 |
| C7 | Br | H | H | Br | 3,5-dichloro-phenyl- | — |

TABLE D

Compounds of formula (Va')

(Va')

| Compound No. | Y¹ | Y² | Y³ | Y⁴ | Q² | $^1$H-NMR (CDCl$_3$, 400 MHz) in ppm |
|---|---|---|---|---|---|---|
| D1 | Me | H | H | Me | 4-methoxy-phenyl- | 0.07 (s, 18H); 2.22 (s, 6H); 3.82 (s, 3H); 6.96 (d, 2H); 7.01 (s, 2H); 7.35 (d, 2H). |
| D2 | Me | H | H | Me | 4-trifluoromethyl-phenyl- | 0.08 (s, 18H); 2.26 (s, 6H); 7.07 (s, 2H); 7.60 (s, 4H). |
| D3 | Me | H | H | Me | 4-chloro-phenyl- | 0.07 (s, 18H); 2.22 (s, 6H); 7.06 (s, 2H); 7.30 (d, 2H); 7.41 (d, 2H). |
| D4 | Me | H | H | Me | 4-fluoro-phenyl- | 0.07 (s, 18H); 2.23 (s, 6H); 7.03 (t, 2H); 7.06 (s, 2H); 7.43 (dd, 2H). |
| D5 | Me | H | H | Me | 3-fluoro-phenyl- | 0.07 (s, 18H); 2.23 (s, 6H); 6.99-7.07 (m, 1H); 7.07 (s, 2H); 7.19-7.33 (m, 3H). |
| D6 | Me | H | H | Me | phenyl- | 0.07 (s, 18H); 2.22 (s, 6H); 7.10 (s, 2H); 7.32-7.37 (m, 3H); 7.42-7.50 (m, 2H). |

Biological Examples

This Example illustrates the pesticidal/insecticidal properties of compounds of formula (I). The tests were performed as follows:

*Spodoptera littoralis* (Egyptian Cotton Leafworm):
Cotton leaf discs were placed on agar in a 24-well microtiter plate and sprayed with test solutions at an application rate of 200 ppm. After drying, the leaf discs were infested with 5 μl larvae. The samples were checked for mortality, feeding behavior and growth regulation 3 days after treatment (DAT). The following compounds gave at least 80% control of *Spodoptera littoralis*: A6, A7, A8, A12, A13, A18, A19, A20, A23.

*Heliothis virescens* (Tobacco Budworm):
Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality and growth regulation. The following compounds gave at least 80% control of *Heliothis virescens*: A6, A7, A8, A10, A12, A13, A14, A18, A19, A20, A22.

*Plutella xylostella* (Diamond Back Moth):
A 24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.
The following compounds gave at least 80% control of *Plutella xylostella*: A2, A6, A7, A12, A13, A18, A19, A23.

*Diabrotica balteata* (Corn Root Worm):
A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.
The following compounds gave at least 80% control of *Diabrotica balteata*: A6, A12, A13.

Compound Nos. A1, A3, A4, A5, A9, A11, A15-A17, and A21 of Table A were tested using the same protocols and showed little or no damage to the test organisms under the test conditions.

The invention claimed is:

1. A compound of formula (I):

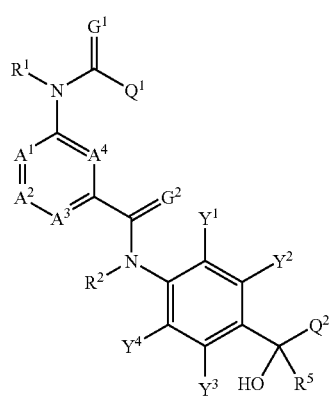

(I)

wherein
$A^1, A^2, A^3$ and $A^4$ are C—X;
each X is independently hydrogen, halogen, cyano, $C_1$-$C_4$alkyl, $C_1$-$C_4$haloalkyl or $C_1$-$C_4$alkoxy;
$R^1$ and $R^2$ are independently of one another hydrogen, $C_1$-$C_4$alkyl or $C_1$-$C_4$alkylcarbonyl-;
$G^1$ and $G^2$ are oxygen;
$Q^1$ is aryl or aryl substituted by one to five substituents $R^3$, which may be the same or different, or $Q^1$ is heterocyclyl or heterocyclyl substituted by one to five substituents $R^3$, which may be the same or different;
$Q^2$ is aryl or aryl substituted by one to five substituents $R^4$, which may be the same or different, or $Q^2$ is heterocyclyl or heterocyclyl substituted by one to five substituents $R^4$, which may be the same or different;
each $R^3$ is independently halogen, cyano, nitro, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halocycloalkyl, hydroxy, $C_1$-$C_3$alkoxy, $C_1$-$C_3$haloalkoxy, $C_1$-$C_3$alkylthio-, $C_1$-$C_3$haloalkylthio-, $C_1$-$C_3$alkylsulfinyl-, $C_1$-$C_3$haloalkylsulfinyl-, $C_1$-$C_3$alkylsulfonyl-, $C_1$-$C_3$haloalkylsulfonyl-, N—$C_1$-$C_4$alkylamino-, N,N-di-($C_1$-$C_4$alkyl)amino-, $C_1$-$C_4$alkylcarbonyl-, $C_1$-$C_4$alkylcarbonyloxy-, $C_1$-$C_4$alkoxycarbonyl-, $C_1$-$C_4$alkylcarbonylamino- or phenyl;
each $R^4$ is independently halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halocycloalkyl, hydroxy, $C_1$-$C_3$alkoxy or $C_1$-$C_3$haloalkoxy;
$R^5$ is $C_1$-$C_4$ perfluoroalkyl;
$Y^1$ and $Y^4$ are independently of each other halogen, cyano, $C_1$-$C_4$alkyl, $C_1$-$C_4$haloalkyl, $C_1$-$C_4$alkoxy-$C_1$-$C_4$alkyl-, $C_1$-$C_3$alkylthio-, $C_1$-$C_3$haloalkylthio-, $C_1$-$C_3$alkylsulfinyl-, $C_1$-$C_3$haloalkylsulfinyl-, $C_1$-$C_3$alkylsulfonyl- or $C_1$-$C_3$haloalkylsulfonyl-; and
$Y^2$ and $Y^3$ are independently of each other hydrogen, halogen or $C_1$-$C_4$alkyl;
or a salt or N-oxide thereof.

2. A compound according to claim 1 wherein each X is independently hydrogen, halogen, cyano, methyl, trifluoromethyl or methoxy.

3. A compound according to claim 1 wherein $R^1$ is hydrogen, methyl, ethyl or acetyl.

4. A compound according to claim 1 wherein $R^2$ is hydrogen, methyl, ethyl or acetyl.

5. A compound according to claim 1 wherein $R^5$ is trifluoromethyl.

6. A compound according to claim 1 wherein $Q^1$ is aryl or aryl substituted by one to five substituents $R^3$, which may be the same or different, or $Q^1$ is heteroaryl or heteroaryl substituted by one to five substituents $R^3$, which may be the same or different.

7. A compound according to claim 1 wherein $Q^2$ is aryl or aryl substituted by one to five substituents $R^4$, which may be the same or different, or $Q^2$ is heteroaryl or heteroaryl substituted by one to five substituents $R^4$, which may be the same or different.

8. A compound according to claim 1 wherein $Y^1$ is halogen, cyano, methyl, ethyl, methoxymethyl or trifluoromethyl.

9. A compound according to claim 1 wherein $Y^2$ is hydrogen, fluoro, chloro or methyl.

10. A compound according to claim 1 wherein $Y^3$ is hydrogen, fluoro, chloro or methyl.

11. A compound according to claim 1 wherein $Y^4$ is halogen, cyano, methyl, ethyl or trifluoromethyl.

12. A compound of formula (II')

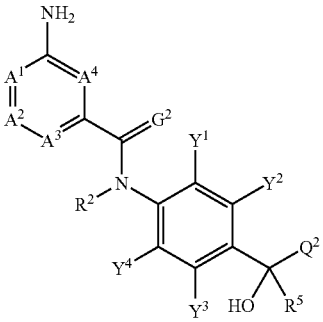

(II')

wherein $A^1, A^2, A^3, A^4, R^2, R^5, G^2, Q^2, Y^1, Y^2, Y^3$ and $Y^4$ are as defined in claim 1; or a salt or N-oxide thereof; or a compound of formula (IV)

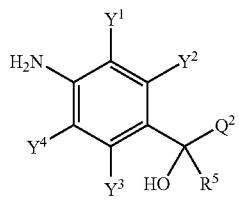

(IV)

wherein $R^5, Q^2, Y^1, Y^2, Y^3$ and $Y^4$ are as defined in claim 1; or a salt or N-oxide thereof; or a compound of formula (V)

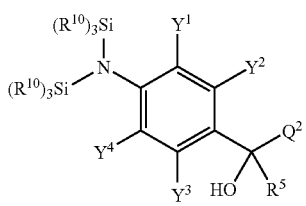

(V)

wherein $R^{10}$ is $C_1$-$C_6$alkyl, and $R^5, Q^2, Y^1, Y^2, Y^3$ and $Y^4$ are as defined in claim 1; or a salt or N-oxide thereof.

13. An insecticidal, acaricidal, nematicidal or molluscicidal composition comprising an insecticidally, acaricidally, nematicidally or molluscicidally effective amount of a compound of formula (I) as defined in claim 1.

* * * * *